United States Patent [19]

Pilipovich et al.

[11] 4,120,904
[45] Oct. 17, 1978

[54] SYNTHESIS OF FLUOROTRINITROMETHANE

[75] Inventors: Donald Pilipovich, Agoura; Louis R. Grant, Jr., Los Angeles; Richard D. Wilson, Canoga Park, all of Calif.

[73] Assignee: The United States of America as represented by the Secretary of the Air Force, Washington, D.C.

[21] Appl. No.: 801,453

[22] Filed: May 26, 1977

[51] Int. Cl.$^2$ ............................................. C07C 79/12
[52] U.S. Cl. .................................................. 260/644
[58] Field of Search ......................................... 260/644

[56] References Cited

U.S. PATENT DOCUMENTS 3,441,619   4/1969   Garner et al. ......................... 260/644

Primary Examiner—Leland A. Sebastian
Attorney, Agent, or Firm—Joseph E. Rusz; Cedric H. Kuhn

[57] ABSTRACT

In the synthesis of fluorotrinitromethane by reacting tetranitromethane with an adduct of an alkali metal fluoride and a fluorinated or chlorofluorinated acetone in an aprotic dipolar solvent, chlorine or bromine is added during the reaction so as to eliminate side reactions.

10 Claims, No Drawings

SYNTHESIS OF FLUOROTRINITROMETHANE

RIGHTS OF THE GOVERNMENT

The invention described herein may be manufactured and used by or for the Government of the United States for all governmental purposes without the payment of any royalty.

FIELD OF THE INVENTION

This invention relates to a process for synthesizing fluorotrinitromethane.

BACKGROUND OF THE INVENTION

In U.S. Pat. No. 3,419,625, R. C. Doss discloses a method for preparing fluorotrinitromethane. As described in this patent, a solution is formed in a reaction zone by dissolving an alkali metal fluoride in a polar organic solvent. Trinitromethane is then slowly added to the solution while maintaining the solution at a temperature in the range of zero to 100° C., preferably within the range of zero to 30° C. After addition of the tetranitromethane is completed, the reaction mixture is maintained at a temperature within one of the aforementioned ranges for a period of about 0.5 to 100 hours. It is stated that when the temperature has been maintained within the preferred range of zero to 30° C., it is then usually desirable to increase the temperature substantially for a short period of time. While the method described is suitable for preparing fluorotrinitromethane, it appears from the patent that it is only effective in producing the product in low yields. Thus, the maximum yield of fluorotrinitromethane obtained in the runs described in the examples was about 9 percent.

In copending U.S. Pat. application Ser. No. 513,630, filed on Oct. 9, 1974, by one of us, there is disclosed a process whereby fluorotrinitromethane can be prepared in high yields. Broadly speaking, the process comprises the step of reacting tetranitromethane with an adduct of an alkali metal fluoride and a fluorinated or chlorofluorinated acetone in the presence of an aprotic solvent. In carrying out this reaction, an alkali metal nitrite is produced as a by-product. A secondary reaction occurs between the nitrite and the fluorotrinitromethane or tetranitromethane, thereby reducing the conversions and yields. While the process disclosed in the application does produce fluorotrinitromethane in high yields, it would be desirable to eliminate the undesirable by-product so as to obtain even higher yields.

It is an object of this invention, therefore, to provide a process for synthesizing fluorotrinitromethane whereby an undesirable by-product formed during the synthesis is eliminated or substantially reduced.

Another object of the invention is to provide an improvement in a process for preparing fluorotrinitromethane whereby the product yield is increased.

Other objects and advantages of the invention will become apparent to those skilled in the art upon consideration of the accompanying disclosure.

SUMMARY OF THE INVENTION

The present invention resides in an improvement in a process for preparing fluorotrinitromethane in which tetranitromethane is reacted with an adduct of an alkali metal fluoride and a fluorinated or chlorofluorinated acetone in the presence of an aprotic solvent. Broadly speaking, the improvement comprises the step of reacting tetranitromethane with the adduct in the presence of chlorine or bromine. As a result of the presence of the chlorine or bromine, side reactions that normally occur between alkali metal nitrite by-product and the reactants are eliminated with a concomitant increase in product yield.

In conducting the process of this invention, initially the adduct is formed by adding the alkali metal fluoride and the fluorinated or chlorofluorinated acetone to the aprotic solvent. The reaction that occurs in this step of the process can be represented by the following equation:

$$MF + (CF_{3-x}Cl_x)_2CO \xrightarrow{Solvent} MOCF(CF_{3-x}Cl_x)_2 \quad (1)$$

According to the process disclosed in application Ser. No. 513,630, tetranitromethane is added to the solution after formation of the adduct. The reaction that occurs is shown by the following equation:

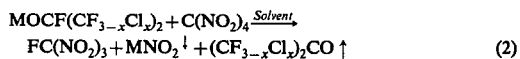

$$MOCF(CF_{3-x}Cl_x)_2 + C(NO_2)_4 \xrightarrow{Solvent}$$
$$FC(NO_2)_3 + MNO_2\downarrow + (CF_{3-x}Cl_x)_2CO\uparrow \quad (2)$$

In the reaction depicted by equation (2), an alkali metal nitrite ($MNO_2$) is formed as a by-product. A secondary reaction occurs between the nitrite by-product and the tetranitromethane or the fluorotrinitromethane. As a result of these side reactions, there is a substantial diminution of product yield. It has been discovered that the undesired alkali metal nitrite can be removed with the elimination of the side reactions by conducting the reaction shown in equation (2) in the presence of chlorine or bromine. The reaction that occurs when chlorine is added is shown by the following equation:

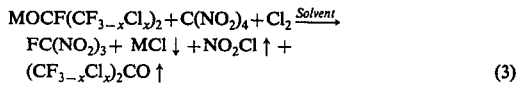

$$MOCF(CF_{3-x}Cl_x)_2 + C(NO_2)_4 + Cl_2 \xrightarrow{Solvent}$$
$$FC(NO_2)_3 + MCl\downarrow + NO_2Cl\uparrow +$$
$$(CF_{3-x}Cl_x)_2CO\uparrow \quad (3)$$

From equation (3) it is seen that the undesirable nitrite by-product is eliminated by reacting with chlorine (or bromine) as it forms. The reaction products that form in this reaction, i.e., MCl and $NO_2Cl$, do not enter into secondary reactions with the tetranitromethane or fluorotrinitromethane.

In carrying out the reaction shown by equation (3), it is necessary to have the requisite amount of chlorine or bromine present during the period of reacting the adduct and the tetranitromethane. The presence of chlorine or bromine during this period is essential in order that the alkali metal nitrite may be oxidized as it is formed. In the preferred procedure, therefore, a portion of an inert carrier gas and chlorine or bromine is introduced into the solution of the adduct $[MOCF(CF_{3-x}Cl_x)_2]$, prepared as described above, prior to addition of the tetranitromethane. Thereafter, the tetranitromethane is added and flow of the inert carrier gas and chlorine or bromine is continued until the reaction is completed.

In the foregoing equations, M is an alkali metal and $x$ is zero to 2, inclusive. Examples of alkali metals include sodium, potassium, cesium and rubidium. It is often preferred to employ potassium fluoride and hexafluoroacetone in forming the adduct. However, other fluorides, such as cesium and rubidium fluorides, and other acetones, such as tetrafluorodichloro- and difluorotetrachloroacetones, can be employed. Use of the adduct permits the fluorination to proceed in a homogeneous manner while the presence of chlorine or bromine eliminates or substantially reduces the formation of undesirable alkali metal nitrite by-product. In addition to improved product yields, there is a definite advantage in the short reaction times that are required.

Examples of aprotic solvents that can be employed include N,N-dimethylformamide, acetonitrile, diglyme [bis(2-methoxyethyl)ether], and the mono-, tri- and tetraglymes.

As mentioned above, the adduct or complex is formed by adding an alkali metal fluoride and a fluorinated or chlorofluorinated acetone to an aprotic solvent. When forming the adduct, substantially equimolar amounts of anhydrous fluoride and the acetone are added to anhydrous solvent. In a preferred procedure for preparing the adduct, the acetone is bubbled into a suspension of alkali metal fluoride in the solvent, thereby providing a solution of the adduct. Formation of the adduct can be conveniently carried out at ambient temperature.

In a preferred procedure, chlorine or bromine is flowed into the solution after formation of the adduct. This is preferably accomplished by bubbling a mixture of the chlorine or bromine and an inert carrier gas into the solution. The amount of chlorine or bromine passed into the solution is only a fraction, e.g., about 5 to 15 percent, of the total amount, the remainder being added after introduction of the tetranitromethane. The chlorine or bromine is added to the adduct solution prior to charging of the tetranitromethane in order to ensure its presence in the reaction zone when the basic reaction commences.

Any suitable inert gas can be employed as the carrier gas, examples of which include nitrogen, helium and argon. The mole ratio of inert gas to chlorine or bromine can vary over a wide range, e.g., from 20:1 to 1:20.

After introduction of chlorine or bromine into the adduct solution, the tetranitromethane is added. In this step of the process wherein tetranitromethane is converted to fluorotrinitromethane, the alkali metal fluoride of the adduct functions as a fluorinating agent. The fluorinated or chlorofluorinated acetone that complexes with the fluoride acts as a catalyst in the fluorination of tetranitromethane. The mole ratio of adduct [MOCF($C_{3-x}Cl_x$)$_2$] to tetranitromethane [C(NO$_2$)$_4$] generally falls in the range of 1:10 to 2.5:1. Molar concentrations usually range from 0.1 to 2.2 molar MOCF($C_{3-x}Cl_x$)$_2$ and from 0.1 to 5 molar C(NO$_2$)$_4$. The reaction is conducted under anhydrous conditions at a temperature in the range of about −15° to 40° C. The reaction pressure usually ranges from 1 mm of mercury or less to 760 mm of mercury.

The introduction of chlorine or bromine is continued during the reaction of the adduct with the tetranitromethane. In general, the reaction times range from about 10 to 60 minutes. However, a period from about 15 to 30 minutes is usually sufficient to complete the reaction of the adduct and tetranitromethane. And because of the short reaction time, it is essential to have the requisite amount of chlorine or bromine present during this time so as to oxidize the alkali metal nitrite formed. Accordingly, as described above, a portion of the chlorine or bromine is preferably added to the adduct solution in order to ensure its presence when the basic reaction commences.

A more comprehensive understanding of the invention can be obtained by referring to the following illustrative examples which are not intended, however, to be unduly limitative of the invention.

EXAMPLE I

A run was conducted in which chlorine diluted with nitrogen was bubbled through a saturated solution of sodium nitrite in N,N-dimethylformamide (DMF). Examination of the trapped exit gases showed a mixture of NO$_2$Cl, NO$_2$ and Cl$_2$.

The data obtained in the run indicate that the chlorine reacted with the sodium nitrite in solution in DMF.

EXAMPLE II

A series of runs was conducted in which fluorotrinitromethane was synthesized. Run 1 was a control run in which chlorine was not added while runs 2 and 3 were carried out in accordance with the present invention.

Initially a solution of KOCF(CF$_3$)$_2$ [2.2 molar] in N,N-dimethylformamide (DMF) was formed. This was accomplished by bubbling (CF$_3$)$_2$CO into a suspension of anhydrous KF in anhydrous DMF.

In run 1 (control), 5 ml of 2.2 molar KOCF(CF$_3$)$_2$ in anhydrous DMF was added to a reaction vessel and diluted to 5.0 ml with anhydrous DMF. The reaction vessel consisted of a 50 ml round-bottom, three-neck flask which was equipped with a dropping funnel, an inlet tube with a safety trap, and an exit tube with a −80° C. cooled trap. Tetranitromethane (1.0 g, 5.10 mmoles) was placed in the dropping funnel and diluted with 10 ml of DMF. The system was flushed with nitrogen at 40 cc/min for 2 to 3 minutes. The C(NO$_2$)$_4$—DMF solution was added to the KOCF(CF$_3$)$_2$ at ambient temperature. Fluorotrinitromethane yields and tetranitromethane conversions were obtained by gas-liquid chromatographic analyses of the reaction mixture as a function of reaction time.

In runs 2 and 3, the same quantities of reactants as used in run 1 were employed. After flushing the reaction vessel with nitrogen, a gas stream of chlorine (8 cc/min) and nitrogen (40 cc/min) was passed through the DMF solution of KOCF(CF$_3$)$_2$ for about 2 minutes. The C(NO$_2$)$_4$ solution was then added and in run 2 the flow of chlorine and nitrogen was continued for a total of 16 minutes. In run 3 the flow of chlorine and nitrogen was continued for a total of 30 minutes. As in run 1, the reaction mixtures of runs 2 and 3 were analyzed for FC(NO$_2$)$_3$ and C(NO$_2$)$_4$ as a function of time.

The results obtained in the runs are set forth below in the table.

Table

| Run No. | Molar[1] Ratio (CF$_3$)$_2$- CFO$^-$K$^+$ TNM | Reaction Time, hrs | Chlorine, mmoles | FTM[2] Conversion[3] % | Yield[4] % | TNM Conversion, %[5] |
|---|---|---|---|---|---|---|
| 1 | 2.2 | 0.25 | 0 | 43 | 69 | 95 |
|   |     | 0.50 |   | 41 | 62 | 100 |
|   |     | 1.0  |   | 24 | 32 | 100 |
| 2 | 2.2 | 0.25 | 6 | 53 | —  | —  |
|   |     | 0.50 |   | 59 | —  | —  |
|   |     | 1.0  |   | 63 | 73 | 86 |
| 3 | 2.2 | 0.25 | 11 | 55 | 68 | 80 |

Table-continued

| Run No. | Molar[1] Ratio $(CF_3)_2$- $CFO^-K^+$ / TNM | Reaction Time, hrs | Chlorine, mmoles | FTM[2] Conversion[3] % | Yield[4] % | TNM Conversion, %[5] |
|---|---|---|---|---|---|---|
|  |  | 0.50 |  | 65 | 73 | 88 |
|  |  | 1.0 |  | 66 | 73 | 91 |

[1]TNM = tetranitromethane - $C(NO_2)_4$
[2]FTM = fluorotrinitromethane - $FC(NO_2)_3$
[3]Percentage of TNM converted to FTM
[4]Yield = $\frac{\text{mmoles of FTM}}{\text{mmoles of TNM converted to FTM}} \times 100$
[5]Percentage of TNM converted From the data in the foregoing table, it is seen that by conducting the reaction between the adduct and tetranitromethane in the presence of chlorine higher conversions of tetranitromethane to fluorotrinitromethane and concomitantly higher product yields are obtained. Thus, the data demonstrate that the chlorine by removing undesirable potassium nitrite by-product is effective in eliminating or substantially reducing side reactions between the nitrite and the tetranitromethane or fluorotrinitromethane.

As will be evident to those skilled in the art, modifications of the present invention can be made in view of the foregoing disclosure without departing from the spirit or scope of the invention.

We claim:

1. In a process for preparing fluorotrinitromethane in which tetranitromethane is reacted in an aprotic solvent with a complex having the following formula:
   $MOCF(CF_{3-x}Cl_x)_2$, wherein M is an alkali metal and x is zero to 2, inclusive, the improvement which comprises conducting the reaction in the presence of chlorine or bromine.

2. The process according to claim 1 in which the amount of chlorine or bromine ranges from about 0.1 to 2 moles per mol of tetranitromethane.

3. The process according to claim 2 in which the reaction is conducted under anhydrous conditions for a period of about 10 to 60 minutes at a temperature in the range of about $-15°$ to $40°$ C. and at a pressure ranging from about 1 mm to 760 mm of mercury.

4. The process according to claim 3 in which the mole ratio of the complex to tetranitromethane is in the range of 1:10 to 2.5:1.

5. The process according to claim 4 in which the solvent is a member selected from the group consisting of N,N-dimethylformamide, monoglyme, diglyme, triglyme, tetraglyme, and acetonitrile.

6. A process for preparing fluorotrinitromethane which comprises flowing chlorine or bromine in an inert carrier gas into a solution of a complex in an aprotic solvent contained in a reaction zone, the complex having the following formula:
   $MOCF(CF_{3-x}Cl_x)_2$ wherein M is an alkali metal and x is zero to 2, inclusive; and introducing tetranitromethane into the reaction zone while continuing to flow chlorine or bromine in an inert carrier gas into the zone, the tetranitromethane and the complex reacting therein in the presence of chlorine or bromine to form fluorotrinitromethane.

7. The process according to claim 6 in which the total amount of chlorine or bromine flowed into the reaction zone ranges from about 0.1 to 2 moles per mole of tetranitromethane.

8. The process according to claim 7 in which about 5 to 15 percent of the total amount of chlorine or bromine is flowed into the solution of the complex prior to introduction of the tetranitromethane.

9. The process according to claim 8 in which the mole ratio of inert carrier gas to chlorine or bromine is in the range of 20:1 to 1:20.

10. The process according to claim 9 in which the inert carrier gas is nitrogen, argon or helium.

* * * * *